United States Patent [19]

Bush

[11] 3,984,274

[45] Oct. 5, 1976

[54] MEANS AND METHOD OF MANUFACTURING BAGS FOR BREATHING APPARATUS

[75] Inventor: John Bush, Los Alamitos, Calif.

[73] Assignee: General Connectors Corporation, Burbank, Calif.

[22] Filed: Jan. 10, 1975

[21] Appl. No.: 539,944

Related U.S. Application Data

[62] Division of Ser. No. 427,676, Dec. 26, 1973, Pat. No. 3,902,654.

[52] U.S. Cl. .............................. 156/297; 93/8 VB; 93/35 R; 93/35 PC; 128/202; 156/227; 156/304; 156/443; 156/492; 156/580

[51] Int. Cl.² ...................... B32B 1/10; B32B 17/10; B32B 25/20; B32B 27/28

[58] Field of Search ........... 100/11; 229/56; 138/37, 138/42, 38; 93/35 PC, 35 R, 8 VB, 8 R, 12 R; 156/227, 297, 443, 471, 475, 492, 583, 580, 157, 304, 212, 221; 128/202, 212, 142.6

[56] References Cited
UNITED STATES PATENTS

| | | | |
|---|---|---|---|
| 693,795 | 2/1902 | Giersberg | 128/202 X |
| 1,213,160 | 1/1917 | Davis | 128/202 |
| 1,375,365 | 4/1921 | Clark | 156/583 |
| 3,342,653 | 9/1967 | Schnitzer | 156/297 X |
| 3,475,260 | 10/1969 | Stokes | 156/157 X |
| 3,530,773 | 9/1970 | Kuhnle et al. | 93/12 R |

FOREIGN PATENTS OR APPLICATIONS

| | | | |
|---|---|---|---|
| 458,538 | 12/1936 | United Kingdom | 128/202 |

*Primary Examiner*—Douglas J. Drummond
*Assistant Examiner*—Thomas Bokan
*Attorney, Agent, or Firm*—Lyon & Lyon

[57] ABSTRACT

A bag for breathing apparatus having an internal zig-zag passageway between an inlet and an outlet, the bag being formed of flexible material presenting an interior surface of silicone rubber and an exterior surface of a fluoroelastomer based on a copolymer of vinylidene and hexafluoropropylene the means and method of manufacture involving a mounting plate which carries supporting panels for the end wall and partition wall components of the bag, the side walls and bottom wall components of the bag being held in contact with selected margins of the components supported on the panels by a foldable external retaining structure to permit heating of the bag components to a bonding temperature or to permit setting of appropriate adhesive.

5 Claims, 10 Drawing Figures

MEANS AND METHOD OF MANUFACTURING BAGS FOR BREATHING APPARATUS

This is a division, of application Ser. No. 427,676, filed Dec. 26, 1973 now U.S. Pat. No. 3,902,654.

BACKGROUND OF THE INVENTION

A type of breathing apparatus which is carried by the user and which is isolated from ambient air, requires a relatively long passageway between parts of the apparatus to permit the recirculating air therein to cool to breathing temperature. In order to arrange the passageway in a compact manner, the passageway is folded in a zigzag manner. This may be accomplished by providing an essentially rectangular bag having partial partitions. Construction of such a bag poses problems. A further problem concerns the fact that the surface of the passageway and the exterior surface of the bag must be of different materials.

The present invention is a solution to these problems.

SUMMARY OF THE INVENTION

The means and method of manufacturing bags for breathing apparatus is summarized in the following objects:

First, to provide a means and method of manufacturing a bag for breathing apparatus wherein the bag is provided with a zigzag passageway formed of flexible material, the inner surfaces being of a material which is inert to fluids passing therethrough and an external surface which forms a barrier to surrounding contaminents.

Second, to provide a means and method for manufacturing a bag, as indicated in the preceding object wherein all of the components of a bag structure may be bonded together in a single operation.

Third, to provide a means and method which utilizes a novelly arranged frame structure including a mounting member on which are removably mounted a series of bag end positioning and bag partition positioning panels, and novelly arranged external members for holding the sides and bottom of the bag in position for bonding connection with the ends and partitions of the bag.

Fourth, to provide a means and method which permits utilization of flexible laminated material having a core of reinforcing fabric and surface laminations of different material bonded to the fabric core.

The bag manufactured by the present means and method is designed specifically for an air breathing apparatus which requires a relatively long air passageway. The bag permits a more compact passageway by arranging the passageway as a zigzag or folded passageway. The breathing apparatus includes an air outlet tube 1 and an air inlet tube 2 joined by a connecting closure 3 and is not a part of the present invention.

Figure 7:
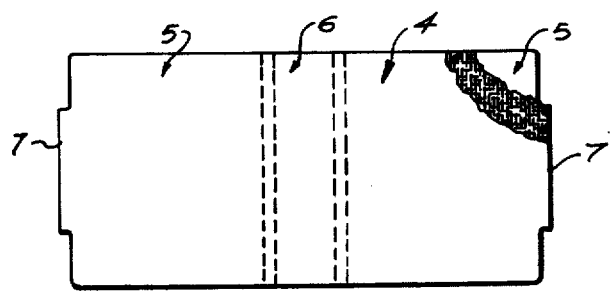
FIGS. 7, 8, 9 and 10 are reduced developed views of various components of the bag.
Figure 8:
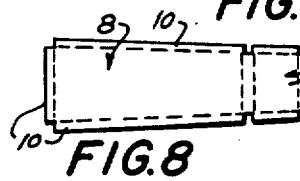

The bag structure includes a major covering 4, a developed view of which is shown in FIG. 7 and includes a pair of side wall components 5, a bottom wall component 6 and border flanges 7. The bag structure also includes a pair of end wall components 8, a developed view of which is shown in FIG. 8. Each end wall component is provided with a top extension 9 and the margins are provided with flanges 10.

Figure 9:
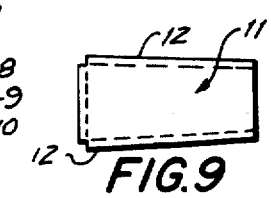
Figure 10:
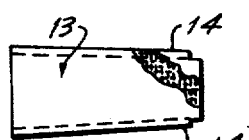

The bag structure further includes a central partition component 11 having marginal flanges 12, a developed view of which is shown in FIG. 9. Also provided are lateral partition components 13 having marginal flanges 14 as shown in the developed view of FIG. 10.

Construction of the bag is accomplished by an interior positioning structure which includes a mounting plate 15 on which are mounted a pair of end wall positioning panels 16, each of which includes a vertical member 17 and a horizontal member 18, the latter supported by a mounting bracket 19 the members are joined by bolts in such a manner that they may be disassembled.

The mounting plate also supports a central partition positioning panel 20 having a mounting bracket 21 also bolted so as to be removable. Between the panels 16 and the central panel 20 is a pair of lateral partition positioning panels 22 suitably bolted to the mounting plate by mounting brackets 23.

An exterior retaining structure is also provided which includes a pair of side plates 24 and a bottom plate 25 joined by hinges 26. The mounting plate 15 is provided with mounting pedestals 27 which receive clamp screws 28 for engagement with cross bars 29 provided along the margins of the side plates 24 remote from the bottom plate 25. In this connection it should be noted that the positioning and the retaining structures are inverted so that the bag is formed bottom side uppermost.

The components of the bag structure including the major covering and end wall components are composed of laminated material comprising an inner lamination 30 of silicone rubber, an outer lamination 31 formed of a fluoroelastomer based on a copolymer of vinylidene, fluoride and hexafluoropropylene under the trade name of VITON. Interposed inbetween the laminations 30 and 31 is a central lamination 32 of glass fiber cloth.

The material is formed by applying a thin coating of the fluoroelastomer to one side of the glass fiber cloth curing the same, then applying a coat of the silicone rubber to the other side of the glass fiber cloth, then curing the silicone rubber.

The laminations comprising the internal walls formed by the partition components 11 and 13 comprise surface laminations 33 of silicone rubber and a central lamination 34 of glass fiber cloth. In this case the silicone rubber is applied as a coating on one side, then partially secured to permit handling whereupon the opposite side is coated and the curing is completed.

The method of manufacture is essentially as follows:

The various bag components are assembled on the internal positioning structure, however the order of assembly may vary. More specifically, the end wall components 8 are applied over the positioning panels 6 first however, a coating of silicone adhesive as indicated by 35, is applied to the edges of the panels over which the marginal flanges 10 are to be fitted. Also the top extensions 9 are fitted under the horizontal member 18 and a flange, which will form a part of the opening to receive the outlet or the inlet tubes 1 or 2, is applied over a portion of the mounting bracket 19. Similarly, the components 11 and 13 are applied over the panels 20 and 22. The central component 11 is fitted so that a margin extends over the extended end of the panel 20 whereas the lateral components 13 terminate short of the extremities of the panels 22.

Figures 2, 5:
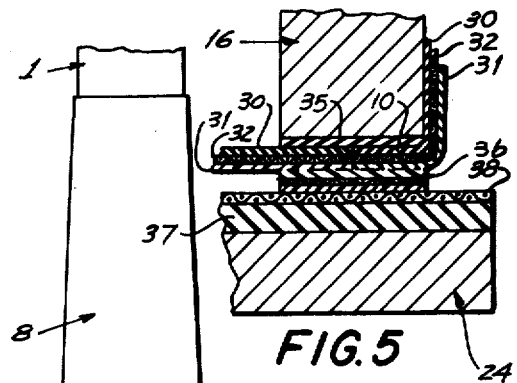
FIG. 2 is an end view thereof.
FIG. 5 is an enlarged fragmentary sectional view taken through 5—5 of FIG. 3 including portions of the bag held between portions of the positioning structure and retaining structure.
Figures 3, 4, 6:
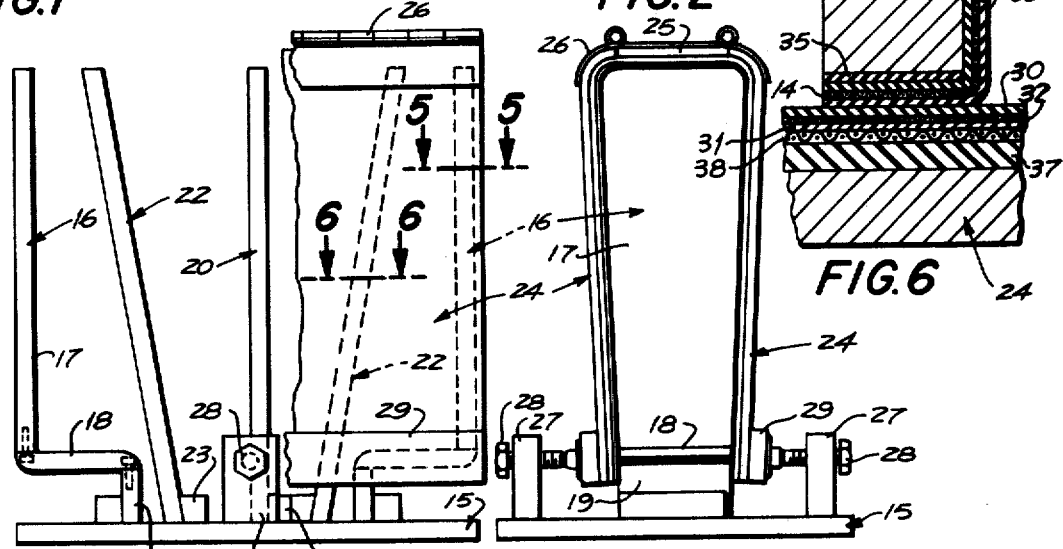
FIG. 3 is a side view of the apparatus for manufacturing the bag with portions shown fragmentarily and with the bag itself omitted.
FIG. 4 is an end view thereof.
FIG. 6 is a similar enlarged fragmentary sectional view taken through 6—6 of FIG. 3.

The major covering 4 including the side wall components 5 and bottom wall component 6 are placed over the edges of the panels 16, 20 and 22. In the case of the panel 16 the margins of the major covering abut the margins of the components 8 as shown in FIG. 5 so that the external surface will be of the same composition, in this case the fluoroelastomer. A laminated reinforcing strip 36 having a fiber glass core and opposed surface laminations of the fluoroelastomer is placed over the abutting margins so as to bond with the abutting margins.

After positioning the major covering the external retaining structure is fitted in place. The interior surface of the external retaining structure 24 is provided with a resilient covering 37 capable of withstanding the curing temperatures. Also, the inner surface is provided with an exposed lamination of fiber glass, indicated by 38 which is not embedded in the underlying coating so as to present a porous surface to permit the escape of gases during the curing cycle. The major covering 4 is held in place by the clamping screws 28 bearing against confronting cross bars 29 which distribute the pressure exerted by the side plates 24. The bag structure is then cured at an appropriate temperature. After curing is completed the external retaining structure is removed and the mounting plate 15 is disconnected so as to provide access to the panels, particularly to divide the end wall positioning panels 16 for removal. The other panels are readily removed without further disassembly. This is true even though the bottom side of the completed bag is of greater width than the top side due to the fact that some stretching of the material may occur.

Figure 1:
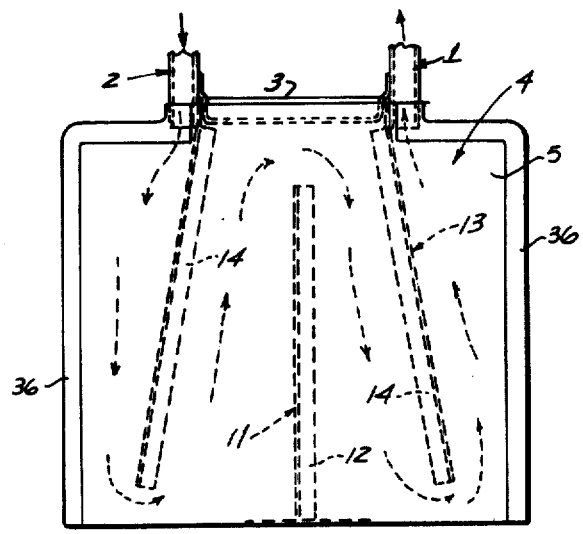
FIG. 1 is a side view of the bag for breathing apparatus.

In the course of forming the bag structure appropriate margins form upturned flanges which receive the outlet tube 1, inlet tube 2 and the connecting closure 3 in such a manner that a zigzag or folded passageway is established therebetween as indicated by the arrows in FIG. 1. More specifically, the air flows downwardly around one of the lateral partition components 13 under this component and then upwardly over the central partition component 11 and finally downwardly around the lower end of the other lateral component 13 for discharge through the outlet tube 1.

Having fully described my invention it is to be understood that I am not limited to the details herein set forth, but that my invention is of the full scope of the appended claims.

I claim:
1. Means for constructing an air bag for breathing apparatus wherein the bag is provided with an inlet, an outlet and a zigzag passageway therebetween formed of partition components surrounded by end wall, side wall and bottom wall components, said means comprising:
   a. a generally horizontal mounting plate;
   b. a plurality of spaced positioning panels secured at their lower edges to the mounting plate and projecting upwardly therefrom whereby end wall components and partition components of the air bag may be placed against the panels with selected margins of the components overlying the corresponding side and upper edges of the panels: said corresponding edges also supporting the side wall and bottom wall components of the bag placed thereover and in contact with said selected margins of the end wall and partition components;
   c. and an exterior retaining structure including members adapted to be placed over the side wall component and bottom wall component of the bag; and means for pressing the retaining structure toward the said edges of the positioning panels to compress the portions of the bag therebetween to effect a bond therebetween.
2. A means as defined in claim 1, wherein:
   a. at least some of the positioning panels are removably secured to the mounting plate to facilitate their subsequent removal from the bag.
3. A means as defined in claim 1, wherein:
   a. the end wall component positioning panels include inwardly offset extensions for top forming components of the bag.
4. A method of constructing an air bag for breathing apparatus formed of heat curable and bondable material wherein the bag is provided with an inlet, an outlet and a zigzag air passage therebetween formed of partition components surrounded by end wall, side wall and bottom components; the method utilizing positioning panels and a confronting exterior retaining structure, said method comprising the steps of:
   a. placing partition and end wall components of said bag on corresponding supporting panels with selected margins in overlapping relation with corresponding edges of the panels;
   b. placing an exterior bag component forming the sidewalls and bottom of the bag over the panels and in contact with the selected margins of the panels;
   c. and pressing the mutually contacting portions of the bag components together by means of said exterior retaining structure, while subjecting the components to heat whereby to effect a bond therebetween,
   d. and removing said support panels.
5. A method as defined in claim 4, including the further step of:
   a. placing reinforcing strips over selected marginal portions of the exterior bag component prior to pressing and heating the bag components for bonding thereto.

* * * * *